United States Patent [19]

Shorr et al.

[11] Patent Number: 5,095,057
[45] Date of Patent: Mar. 10, 1992

[54] HALOBENZYL POLYAMINES AND POLYMERS MADE FLAME RETARDANT THEREWITH

[75] Inventors: Leonard M. Shorr; Many Ravey, both of Haifa, Israel

[73] Assignee: Bromine Compounds Limited, Beer-Sheva, Israel

[21] Appl. No.: 451,450

[22] Filed: Dec. 15, 1989

[30] Foreign Application Priority Data

Dec. 21, 1988 [IL] Israel ............................... 88757

[51] Int. Cl.⁵ ............... C07C 211/13; C07C 211/14; C08G 73/00; C08K 5/17
[52] U.S. Cl. ........................... 524/236; 521/129; 523/461; 524/410; 524/411; 564/366; 528/396
[58] Field of Search ............... 523/461; 564/510, 666, 564/405, 505, 366, 395; 524/236, 410, 411; 521/129; 528/396

[56] References Cited

U.S. PATENT DOCUMENTS

| 2,739,981 | 3/1956 | Szabo et al. | 564/372 |
| 3,308,158 | 3/1967 | Szobel et al. | 564/405 |
| 3,609,190 | 9/1971 | Sobel | 524/236 |
| 3,663,620 | 5/1972 | Merianos et al. | 564/405 |
| 3,960,538 | 6/1976 | Merianos et al. | 71/67 |
| 4,108,906 | 8/1978 | Anderson | 564/366 |
| 4,136,082 | 1/1979 | Brady | 524/236 |

FOREIGN PATENT DOCUMENTS

| 1173649 | 7/1964 | Fed. Rep. of Germany . |
| 762991 | 12/1956 | United Kingdom . |
| 763534 | 12/1956 | United Kingdom . |
| 982268 | 2/1965 | United Kingdom . |

OTHER PUBLICATIONS

CA 87:140778f (1977).
CA 61:10844g (1964).
CA 95:168666 (1981).
Phase Transfer Catalysis, Principles and Techniques, pp. 217-220, Charles M. Starks & Charles Liotta, ed. (1978).
Hackh's Chemical Dictionary-4th edition, pp. 35 and 533.
Chemical Abstract 95, Nov. 1981, No. 168666q.
Merck Index, 11th edition, p. 7541.

Primary Examiner—Veronica P. Hoke
Attorney, Agent, or Firm—Michael N. Meller

[57] ABSTRACT

A new class of compounds, is disclosed, defined by the formula:

$$R'_2N(CH_2CH_2NR'')_yR$$

where R, R' and R'' are equal or different and are

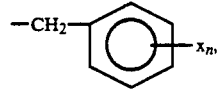

wherein x is bromine or chlorine, n is an integer from 3 to 5 inclusive and y is an integer equal to or greater than 1.

The compounds of the invention are useful as fire retardant agents.

15 Claims, No Drawings

HALOBENZYL POLYAMINES AND POLYMERS MADE FLAME RETARDANT THEREWITH

BACKGROUND OF THE INVENTION

The present invention relates to novel halo-derivative addition compounds useful as flame retardant agents for polymeric compositions, to a process for their preparation and to flame retarded polymer compositions containing said novel compounds. More particularly, the invention relates to novel, halo-derivative addition compounds useful as flame retardant agents and to polymeric compositions containing them.

Halogen-containing compounds are commonly used for the fire retardation of numerous polymeric materials. Such fire retardants, depending on their chemistry, can be applied in two forms, according to whether they are reacted into the polymeric structure or not. In the first case they become permanently incorporated into the polymer structure: fire retardants that behave in this manner will be called "active fire retardants". In the second case they form a mixture with the preformed polymeric material and will be called "additive fire retardants" or briefly "additives".

The use of an additive fire retardant does not involve any chemical interaction between the polymeric substrate and the additive, which is merely dissolved or dispersed in the polymer matrix and therefore can be lost from the substrate in various ways. Typical example of the latter are materials with appreciable vapor pressure which may vaporize out, incompatible materials which bleed and soluble materials which can be leached out. Therefore, it is clear that where the chemical and physical properties of the polymer permit, an active fire retardant is generally preferable.

It is commonly recognized in the field of fire retardant technology that the efficacy of an active fire retardant is greater than that of an additive fire retardant. On the other hand, mere additives are more easily incorporated into the plastic mass and are generally more versatile, both with respect to substrate choice and concentration levels employable. The latter point is particularly important, since fire retardants are often more expensive than the polymer itself and not every application requires the same degree of fire retardation. Thus the amount of additive to be added is optimally variable.

Although the flame retardant polymer compositions obtained by the incorporation of these novel flame retardant agents according to the present invention are by themselves very efficient, one may further enhance their effectiveness by including one or more synergists conventionally used in flame retardation. These synergistic compounds include organo-phosphorus compounds, oxides, sulfides or organic salts of antimony, boron, arsenic or zinc borate. The preferred synergistic compounds for use in the compositions of this invention are organo-phosphorus compounds and antimony oxide.

For some purposes, it might be desirable to incorporate in the polymeric composition an additional flame retardant in order to obtain a particular property. Such additional flame retardants may be e.g. halogenated compounds, such as decabromodiphenyl ether, brominated polystyrene, poly-(pentabromobenzyl acrylate) and dodecachloro-dodecahydrodimethanodibenzocyclooctene, hydrated oxides, such as hydrated alumina and hydrated magnesia, or other commonly employed compounds, such as melamine cyanurate. Also other common plastics ingredients such as fillers, pigments, lubricants, smoke suppressants, plasticisers, antioxidants etc., may be incorporated.

As known in the art, another problem with fire retarded polymeric materials is their enhanced sensitivity to ultraviolet light irradiation, leading to discoloration thereof. Furthermore, a common deficiency in the use of simple additive flame retardants is their tendency to migrate to the surface during fabrication of the finished product, giving rise to a disfiguration called "bloom".

Polymeric flame retardants have been developed in an attempt to take advantage of the positive characteristics of simple additives, yet minimize their deficiencies. Such materials are usually expensive to manufacture and often do not have suitable physico-chemical properties.

SUMMARY OF THE INVENTION

It is an object of the present invention to provide flame retardant agents that are suitable for application as additives to polymeric compositions.

It is another object of this invention to provide fire retardant additives that have high molecular weight, and are therefore stably retained in the polymer matrix, yet are not formed by costly polymerization reactions.

It is a further object to provide such agents that do not cause blooming during fabrication.

It is a still further object to provide such agents that have high thermal stability and do not cause objectionable discoloration when incorporated into thermoplastic polymers which are fabricated at high processing temperatures (e.g. polypropylene and ABS which are processed at temperatures above 200° C.)

It is a still further object to provide such agents which impart UV light stability to the polymeric systems into which they are incorporated and thus avoid discoloration due to UV irradiation.

It is a still further object of the invention to provide a process for the preparation of the said fire retardant agents.

It is a still further object of the invention to provide polymeric compositions comprising a polymeric matrix and an additive and having improved fire resistance, which are thermally stable and stable to UV irradiation, which do not undergo discoloration or blooming and maintain their properties in fabrication and use, not being subject to loss of the additive through bleeding, leaching or in other ways.

Other objects and advantages of the invention will become apparent as the description proceeds.

DETAILED DESCRIPTION OF THE INVENTION

The aforesaid objects are attained according to this invention, by a new class of fire retardant agents, which are novel, previously unknown chemical compounds, defined by the following formula:

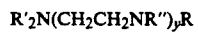

where R, R' and R" are equal or different and are

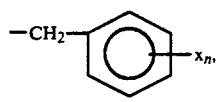

wherein x is bromine or chlorine, n is an integer from 3 to 5 inclusive and y is an integer equal to or greater than 1.

Preferred compounds according to the invention are:

Pentakis-(2,3,4,5,6-pentabromobenzyl)-trichlorobenzyl-TETA
Tetrakis-(2,3,4,5,6-pentabromobenzyl)-EDA
Pentakis-(2,3,4,5,6-pentabromobenzyl)-DETA
Hexakis-(2,3,4,5,6-pentabromobenzyl)-TETA
Heptakis-(2,3,4,5,6-pentabromobenzyl)-TEPA
Poly-(2,3,4,5,6-pentabromobenzyl)-HPA
Tetrakis-(2,3,4,5,6-pentachlorobenzyl)-EDA
Bis-(2,3,4,5,6-pentabromobenzyl)-bis-(2,3,4,5,6-pentachlorobenzyl)-EDA
Tetrakis-(trichlorobenzyl)-EDA
Pentakis-(trichlorobenzyl)-DETA
Hexakis-(trichlorobenzyl)-TETA
Heptakis-(trichlorobenzyl)-TEPA
Poly-(trichlorobenzyl)-HPA
Tris-(2,3,4,5,6-pentabromobenzyl)-trichlorobenzyl-EDA
Pentakis-(2,3,4,5,6-pentachlorobenzyl)-DETA
Hexakis-(2,3,4,5,6-pentachlorobenzyl)-TETA
Heptakis-(2,3,4,5,6-pentachlorobenzyl)-TEPA
Poly-(2,3,4,5,6-pentachlorobenzyl)-HPA etc., and their mixtures.

These compounds can be prepared readily from the corresponding halobenzyl halide and an ethyleneamine. The ethyleneamines are common materials of commerce made by the amination of ethylene dichloride, by which process the following series of compounds is formed (and separated):

Ethylene diamine, EDA
Diethylene triamine, DETA
Triethylene tetramine, TETA
Tetraethylene pentamine, TEPA
Polyamine, HPA.

The reaction between the halobenzyl halide and the ethyleneamine is carried out at elevated temperature, in an organic liquid medium, with or without the presence of an aqueous alkali. When alkali is not present, the product must be liberated from its hydrohalide salt by treatment with aqueous base, for example, sodium hydroxide (conveniently as a 20-50% aqueous solution) or sodium (or potassium) carbonate, or alternatively with alcoholic solutions of sodium (or potassium) alkoxide. Suitable organic liquids which may serve as the reaction medium are hydrocarbons, such as toluene, xylene or petroleum fractions, alcohols such as butanol, isoamyl alcohol and 2-ethylhexanol, polyethylene glycol, cyclohexanol, dimethylformamide and dimethylacetamide.

When alkali is present, it is usually applied in an aqueous concentration of 20-50%. In this case, it is desirable to use a phase transfer catalyst, such as hexadecyltrimethylammonium bromide, tetrabutylammonium sulfate, benzyldimethyldodecylammonium bromide, triethylbenzylammonium bromide, etc. Polyethylene glycol itself may also be used as the catalyst.

The reaction temperature may vary from 90 to 150 degrees C.

It was surprising to find that compounds of the given formula attain the objects of the invention and have the properties hereinbefore described, in spite of the fact that their molecules comprise both amino groups and halogens. Though aromatic halogens are of lower reactivity than aliphatic halogens in amination reactions, they would have been expected to react to an extent deleterious to their application as plastics additives, particularly at the high processing temperatures employed and in the presence of metals present in plastics processing equipment.

It has been known to form N,N,N',N'-tetrabenzylethylenediamine by condensing benzyl chloride with ethylenediamine (Brit. 762,991; CA 51, 17991d [1954]) and to form the corresponding mono-ring chlorinated derivative, either by condensing chlorobenzyl halide with ethylenediamine (EDA) or by the interaction of the corresponding dibenzylamine with ethylene dihalide (Brit. 763,534, CA 51, 17991g [1954]). The non-halogenated N,N,N',N'',N''-pentabenzylderivative of DETA, the chemical name whereof is 1,2-ethanediamine,N-[2-[bis(phenylmethyl)amino]ethyl]-N,N',N'-tris(phenylmethyl)-, is known (Jap. Kok. 76,146,763; CA 87, 140778 [1977]) for the decolorization of dye wastewater. None of these products is a fire retardant.

It has also been known partially to benzylate EDA with trichlorobenzyl chloride to produce biocides (U.S. Pat. No. 3,960,538; CA 85, 77852 [1976]) and an intermediate for an hydroxylated, reactive type fire retardant (Ger. 1,173,649; CA, 61, 10844g [1964]). The benzylation of several secondary amines with pentabromobenzyl bromide has also been reported (Tanaseichuk, et al., CA 95, 168666 [1981]). But no reference has been found to either the preparation or use of compounds represented by the formula given above.

The additives according to the invention are mixed with the polymer matrix by the techniques employed in the art for the use of fire retardant additives. Thus, in the case of thermosetting polymers, if the polymer is used in liquid, oligomeric and/or non-crosslinked form, and is then cured further to polymerize and/or to crosslink, the additive is mixed with the liquid polymeric matrix and this latter is then cured. This technique is used particularly in connection with polyesters, polyurethanes and epoxies. In the case of thermoplastic polymers, the additive may be mixed with the polymer matrix at suitable high temperature, e.g. 200° or more, in a suitable blender. Preferred polymers to which the invention may be applied, are ABS, polystyrene and HIPS, polyolefins such as polypropylene, linear polyesters such as PET and PBT, polyamides such as polycaprolactam, acrylic resins, polyurethanes and epoxy resins. The amount of additive used is preferably such that the polymer composition will contain at least 1% by weight of halogen introduced as the additive.

The invention will now be illustrated by a number of non-limitative examples.

EXAMPLE 1

Synthesis of Pentakis-(2,3,4,5,6-pentabromobenzyl)-trichlorobenzyl-TETA (PPBBTCB-TETA)

Pentabromobenzyl bromide (283 g., 0.5 mole, made by Bromine Compounds Ltd.), trichlorobenzyl chloride (23.00 g., 0.1 mole, unspecified isomer[s], made by Bayer AG), TETA (13.9 g., 0.095 mole, obtained from Aldrich), hexadecyltrimethylammonium bromide, HDTMAB, (0.25 g., obtained from Fluka) as catalyst, NaOH (60 g., 1.5 mole), 60 ml of water and 1.7 liters of toluene were charged to a 3-necked, round bottom flask provided with a mechanical stirrer, thermometer and reflux, condenser. The mixture was stirred vigorously and heated at 100 deg. C for 48 hours. After cooling to ambient temperature, water was added, the mixture was stirred for an additional hour and then filtered.

The combined aqueous layers were concentrated and then made up to one liter standard volume for analysis. Both bromide and chloride were found, 0.48 and 0.09 equivalents respectively, i.e. 96% and 90% recovery of these anions. the solid cake was washed thoroughly on the filter with both toluene (to remove any of the unreacted benzyl halides) and water and then dried at 80 deg. C under vacuum. A gray solid weighing 261 g. was obtained. It contained 72.1% Br, 3.9% Cl and 1.9% N (calc'd. 72.4% Br, 3.8% Cl and 2.0% N).

EXAMPLE 2

Synthesis of Tetrakis-(pentabromobenzyl)-EDA (TPBB-EDA)

The above example was repeated using the following reagents:

Pentabromobenzyl bromide, 113.1 g. (0.2 mole)
EDA hydrate, 4.4 g. (0.055 mole, obtained from Merck)
HDTMAB, 0.9 g.
NaOH, 20 g. (0.5 mole)
$H_2O$, 20 g.
Toluene, 550 ml The mixture was stirred and heated at 98-102 deg. C. for 24 hours. After cooling to room temperature, 1 liter of water was added with stirring for one hour and filtered. The filter cake was washed on the filter with 250 ml of water and 500 ml of toluene and dried (80 deg. C. at 50 mm Hg). A white solid powder was obtained. It contained 78.8% Br and 1.4% N (calc'd. 80.0% Br and 1.4% N). Bromide was recovered in the combined aqueous phases in an amount of 96.7% of that calculated.

Its thermogravimetric analysis (FIG. 1) shows

| a 1% weight loss at 255 Deg. C. | |
|---|---|
| 5% | 260 |
| Major | 300 |

This material was not soluble at the 1% (w/v) level even at reflux in the following solvents:

tetrahydrofuran
dimethylformamide
xylene
toluene
acetic acid
acetic anhydride
acetonitrile
methylene chloride Thus none of these (and similar) solvents can leach this compound out of plastic matrices containing it.

EXAMPLE 3

Polymeric composition containing PPBBTCB-TETA

To 15 g. of a liquid polyester resin (410 Brand, obtained from Fiberplast Ltd.) there were added eight drops of a 7% cobalt octoate solution and 12 drops of methyl ethyl ketone peroxide at ambient temperature. Then, 2.4 g. of PPBBTCB-TETA obtained in Example 1 were added to this homogenous solution with mixing. The mixture was quickly cast into a Teflon mould containing cavities of dimensions 6×100×3 mm. Curing was performed at ambient temperature for 24 hours and then in an oven at 150 deg. C. for 5 hours.

The LOI (Liminting Oxygen Index) of the specimens obtained was measured and compared with that of an identically prepared sample not containing the flame retardant compound of Example 1. The LOI of the PPBBTCB-TETA containing sample was 21.5, whereas that of the control specimen was 19.0.

EXAMPLE 4

ABS polymeric composition containing TPBB-EDA

A comparison study was made between TPBB-EDA and FF-680. The latter material, bis(tribromophenoxy)ethane, is a commercial flame retardant produced by Great Lakes Chemical Corp. It was chosen for this comparison since it is a widely used fire retardant for ABS because of the combination of relatively high values of Heat Distortion Temperatures (HDT), impact energy and light stability.

Compounds were prepared from ABS MB (obtained from Borg-Warner), each of the two fire retardants (at a level of 14% Br contained), and antimony trioxide (Blue Star, obtained from Campine) at a level of Br/Sb of 8/1, in a Brabender Plasticorder at a processing temperature of 200 deg. C., and subjected to the following tests:

Fire retardation by UL-94 with 1.6 mm thick samples
Blooming, visual inspection and sample rubbing between layers of black cloth after exposure for the given number of days at the given temperatures
HDT under a flexural load of 18.5 $kg/cm^2$ according to ASTM D-648-72
Izod notched impact energy according to ASTM D-1822-79 in a pendulum impact tester type 5102 Zwick
Specimens were UV irradiated in a QUV-accelerated weathering tester made by Q-Panel Co. Discoloration (DE) was measured with a Techno Instruments Spectrocolorimeter in comparison with white as reference.

| FR used | UL-94 | Bloom at 65 deg. | Bloom at rm. temp. | HDT deg C. | Impact J/m | UV Ageing DE after 0 hr | UV Ageing DE after 250 hr |
|---|---|---|---|---|---|---|---|
| FF-680 | V-0, 6 sec burn | 66 slight, 100 heavy | 60 heavy | 80 | 49 | 30 | 47 |
| TPBB-EDA | V-0, 0 sec burn | 66 none | 60 none | 84 | 63 | 29 | 41 |

The better performance of TPBBA-EDA with respect to bloom, HDT, impact and UV stability, in addition to fire retardation, is clear from these data.

EXAMPLE 5

HIPS polymeric composition containing TPBB-EDA

This material was compounded in a PLE-651 Plasticorder at 200 degrees C. with the following components, and subsequently press-molded at 200 degrees to produce test specimens:

| Components | % |
|---|---|
| HIPS (Vestyron 638 obtained from Huls) | 82.6 |
| TPBB-EDA | 12.8 |
| Antiox Blue Star "RG" obtained from Campine | 3.6 |
| Mg Stearate obtained from Witco | 0.5 |
| Tinuvin P obtained from Ciba Geigy | 0.5 |
| Bromine content - 10% | - |
| Performance | |
| UL-94 Rating | VO |
| Notched Izod Impact Energy, J/m | 55 |
| HDT, degrees C. | 84 |
| UV irradiation: | |
| DE after exposure hours 0 | 13.4 |
| 250 | 52.1 |

EXAMPLE 6

Synthesis of Mixed Pentabromobenzylated Ethyleneamines (MPE)

A mixture of ethyleneamines obtained from the reaction of ethylene dichloride and ammonia contained the following ratio of constituents:

| EDA | 27 |
|---|---|
| DETA | 12 |
| TETA | 6 |
| TEPA | 3 |
| HPA | 1 |

One (1.0) gram of this mixture (0.031 equivalent) was reacted with 17.5 grams of pentabromobenzyl bromide in refluxing n-butanol for 16 hours. Then a solution of sodium ethoxide (0.04 mole) in ethanol was added (to liberate the product from its hydrobromide salt) and the mixture stirred at 50 degrees C. for another four hours. The solid recovered from this mixture (15 grams) was washed thoroughly with water, dried and found to contain 75.3% Br.

EXAMPLE 7

Inclusion of MPE in a Polyurethane Foam

A sorbitol-based polyether polyol (37.2 g) with an hydroxyl number of 490 mg KOH/g was mixed with 9.6 g MPE, 15.8 g Santicizer 141 (an alkyl-aryl phosphate produced by Monsanto), 0.25 g water, 1.0 g of a silicone surfactant and 1.0 g of dimethylcyclohexylamine as catalyst. Then 15.0 g of Freon 11 were added and the mixture was stirred for 45 seconds. Diphenylmethane diisocyanate (MDI, 51.2 g.) was then added and stirring was continued for 5 seconds more. The mixture was poured into a cardboard box lined with wrapping paper and left to rise freely.

The foam obtained had a Limiting Oxygen Index of 23.5 versus 18.6 for the blank foam, i.e. containing no fire retardant.

EXAMPLE 8

Inclusion of MPE in an Epoxy Resin

The following ingredients were mixed while heating on a water bath:

20.0 g Epoxy Resin (Araldite AW 106, produced by Ciba Geigy)

6.56 g Nadic anhydride [Dicyclo (2,2,1)-5-heptene-2,3-dicarboxylic anhydride], used as hardener 4.39 g MPE Then 0.1 g of N,N-dimethlaniline was added, the mixture was cast into a Teflon mold and heated in an oven at 120 degrees C. for 24 hours.

The Limiting Oxygen Index of the product was 23.2 versus 18.7 for a parallel run without MPE.

EXAMPLE 9

The experiment described in Example 7 was repeated, but the MPE content was reduced to only 0.7 g. The oxygen index of the resulting foam was found to be 21.7 (compared to 18.6 for the blank).

A number of preferred embodiments of the invention have been described for the purpose of illustration, but it will be understood that they are not limitative, that many modifications and adaptations may be made therein, and that the invention may be carried out in other ways without departing from its spirit or exceeding the scope of the claims.

I claim:

1. A halo-derivative addition compound having the formula

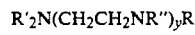

wherein R,R' and R" are the same or different and are

wherein x is bromine or chlorine, n is an integer from 3 to 5 inclusive and y is an integer equal to 1 to 5 inclusive except when $x=Cl$ and $y=1$, then $n=4$ or 5.

2. Compounds according to claim 1, selected from the group consisting of

Pentakis-(2,3,4,5,6-pentabromobenzyl)-trichlorobenzyl-triethylene tetramine,

Tetrakis-(2,3,4,5,6-pentabromobenzyl)-ethylene diamine,

Pentakis-2,3,4,5,6-pentabromobenzyl)-diethylene triamine,

Hexakis-(2,3,4,5,6-pentabromobenzyl)-triethylene tetramine,

Heptakis-(2,3,4,5,-pentabromobenzyl)-tetraethylene pentamine,

Tetrakis-(2,3,4,5,6-pentachlorobenzyl)-ethylene diamine,

Bis-(2,3,4,5,6-pentabromobenzyl-bis-(2,3,4,5,6-pentachlorobenzyl)-ethylene diamine, Tetrakis-(trichlorobenzyl)-ethylene diamine, Pentakis-(trichlorobenzyl)-diethylene triamine, Hexakis-(trichlorobenzyl)-triethylene tetramine, Heptakis-(trichlorobenzyl)-tetraethylene pentamine, Tris-(2,3,4,5,6-pentabromobenzyl)-ethylene diamine, Pentakis-(2,3,4,5,6-pentachlorobenzyl)-diethylene triamine, Hexakis-(2,3,4,5,6-pentachlorobenzyl)-triethylene tetramine, Heptakis-(2,3,4,5,6-pentachlorobenzyl)-tetraethylene pentamine, and mixtures thereof.

3. Flameproofed polymeric compositions, comprising a polymer and at least one of the compounds of claim 1.

4. A composition according to claim 3, wherein the polymer is a thermosetting polymer.

5. A composition according to claim 3, wherein the polymer is a thermoplastic polymer.

6. A composition according to claim 4, wherein the polymer is selected from the group consisting of acrylonitrile-butadiene-styrene copolymer, polystyrene, high impact polystyrene, polyolefins, polyesters, polyamides, acrylic resins, polyurethanes and epoxy resins.

7. A composition according to claim 4, containing at least 1% by weight of halogen introduced as the additive.

8. A composition according to claim 3, also containing, one or more synergists conventionally used in flame retardation.

9. A composition according to claim 8, wherein the synergist is selected from the group consisting of organo-phosphorus compounds and antimony oxide.

10. A flameproofed polymeric composition, comprising a polymer and at least one of the compounds of claim 2.

11. A composition according to claim 10, wherein the polymer is a thermosetting polymer.

12. A composition according to claim 10, wherein the polymer is a thermoplastic polymer.

13. Process for the preparation of a composition according to claim 4, which comprises mixing a thermosetting polymer
and at least one of the compounds of the formula $$R'_2N(CH_2CH_2NR'')_yR$$

wherein R,R' and R" are the same or different and are

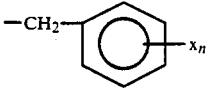

wherein x is bromine or chlorine, n is an integer of from 3 to 5 inclusive and y is an integer equal to or greater than 1, and subsequently curing the resulting mixture to effect or complete cross-linking.

14. Process for the preparation of a composition according to claim 5, which comprises mixing, at high temperatures and under mechanical blending, a thermoplastic polymer
and at least one of the compounds of the formula $$R'_2N(CH_2CH_2NR'')_yR$$

wherein R,R' and R" are the same or different and are

wherein x is bromine or chlorine, n is an integer of from 3 to 5 inclusive and y is an integer equal to or greater than 1.

15. A compound selected from the group consisting of poly-(2,3,4,5,6-pentabromobenzyl)-polyamine, poly(-trichlorobenzyl)-polyamine and poly-(2,3,4,5,6-pentachlorobenzyl)-polyamine when prepared by reacting the apropriate amount of halobenzyl halide with the product of the reaction of ethylene dichloride with ammonia.

* * * * *